(12) United States Patent
Quevedo Enriquez et al.

(10) Patent No.: US 8,946,106 B2
(45) Date of Patent: Feb. 3, 2015

(54) PROCESS FOR THE REGENERATION OF A CATALYST

(75) Inventors: Jose Atilio Quevedo Enriquez, Amsterdam (NL); Leslie Andrew Chewter, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 66 days.

(21) Appl. No.: 13/597,471

(22) Filed: Aug. 29, 2012

(65) Prior Publication Data

US 2013/0225394 A1 Aug. 29, 2013

Related U.S. Application Data

(60) Provisional application No. 61/529,036, filed on Aug. 30, 2011.

(51) Int. Cl.

| | | |
|---|---|---|
| *B01J 20/00* | (2006.01) | |
| *B01J 21/20* | (2006.01) | |
| *B01J 23/90* | (2006.01) | |
| *B01J 25/04* | (2006.01) | |
| *B01J 27/28* | (2006.01) | |
| *B01J 29/90* | (2006.01) | |
| *B01J 31/40* | (2006.01) | |
| *B01J 38/04* | (2006.01) | |
| *B01J 38/12* | (2006.01) | |
| *C07C 1/20* | (2006.01) | |

(52) U.S. Cl.
CPC ... *B01J 29/90* (2013.01); *C07C 1/20* (2013.01)
USPC .................. 502/38; 502/6; 502/20; 502/34

(58) Field of Classification Search
CPC ........... B01J 29/90; C07C 11/04; C07C 11/06
USPC ...................................................... 502/20–56
See application file for complete search history.

(56) References Cited

U.S. PATENT DOCUMENTS

| | | | | |
|---|---|---|---|---|
| 4,198,287 | A * | 4/1980 | Hemler et al. | 208/113 |
| 4,567,029 | A | 1/1986 | Wilson et al. | |
| 6,797,851 | B2 | 9/2004 | Martens et al. | |
| 8,178,741 | B2 * | 5/2012 | Cao et al. | 585/640 |
| 2007/0155999 | A1 | 7/2007 | Pujado et al. | |
| 2007/0203380 | A1 | 8/2007 | Vora et al. | |
| 2013/0225393 | A1 * | 8/2013 | Chewter et al. | 502/6 |
| 2013/0225394 | A1 * | 8/2013 | Quevedo Enriquez et al. | 502/6 |

FOREIGN PATENT DOCUMENTS

WO 2006020083 2/2006

* cited by examiner

*Primary Examiner* — Jennifer A Smith

(57) ABSTRACT

Process for the regeneration of an at least partially coked molecular sieve catalyst comprising introducing the at least partially coked catalyst into a regenerator; introducing into the regenerator an oxygen-containing gas to regenerate at least part of the at least partially coked catalyst, thereby producing a gaseous mixture and at least partially regenerated catalyst; recovering part of the at least partially regenerated catalyst; analysing the at least partially regenerated catalyst to control the burning rate of the coke present on the at least partially coked catalyst in the regenerator by adjusting one or more conditions of the regeneration of the at least partially coked catalyst on the basis of the analysis of the at least partially regenerated catalyst; and separating at least partially regenerated catalyst and at least part of the gaseous mixture as obtained in step (b).

13 Claims, No Drawings

PROCESS FOR THE REGENERATION OF A CATALYST

The present application claims priority to Provisional Application 61/529,036, filed Aug. 30, 2011, which is incorporated herein by reference.

FIELD OF THE INVENTION

This invention relates to a process for the regeneration of a catalyst, in particular a catalyst used in a process for the preparation of olefins such as ethylene and propylene. More in particular this invention relates to a process for regeneration of a catalyst used in the conversion of oxygenates into olefins.

BACKGROUND OF THE INVENTION

Processes for the preparation of olefins are known in the art.

U.S. Pat. No. 6,797,851 describes a process for making ethylene and propylene from an oxygenate feed using two or more zeolite catalysts.

In a first stage, an oxygenate feed is contacted with a first zeolite catalyst containing ZSM-5. The resulting conversion product contains an olefins composition. The olefin composition from the conversion reaction, with or without prior separation of ethylene and propylene, is then contacted with another zeolite catalyst in a second stage. The catalyst of such second stage is a one-dimensional zeolite having 10-membered ring channels, including ZSM-22, ZSM-23, ZSM-35, ZSM-42 or mixtures thereof. The eventual product comprises ethylene, propylene and C4+ olefins. The C4+ olefins may be partly recycled to the first stage as olefinic co-feed of the oxygenate feed.

In such an oxygenate-to-olefins (OTO) process carbonaceous material (coke) will deposit on the catalysts used. As a result the catalysts will deactivate in the course of the process with time, and the catalysts need to be regenerated in order to at least partly remove coke formed on the catalysts. During the regeneration, coke is removed from the catalyst. The extent to which coke is removed from the catalyst is an important feature of the process. If insufficient coke is removed, the selectivity of the oxygenate conversion is affected. However, exposing the catalyst to conditions that remove more coke may lead to an undesired reduction of the catalyst activity. Since the activity, selectivity and life time of a catalyst have a considerable impact on the efficiency and cost-effectiveness of an OTO-process, it would be desirable to have a regeneration process that can contribute significantly to the overall performance of an OTO process.

SUMMARY OF THE INVENTION

A regeneration process is now proposed wherein the burning rate of the coke present on the catalyst to be regenerated is controlled in a particular manner.

Accordingly, the present invention provides a process for the regeneration of an at least partially coked molecular sieve catalyst, which process comprises the steps of:
(a) introducing the at least partially coked catalyst into a regenerator;
(b) introducing into the regenerator an oxygen-containing gas to regenerate at least part of the at least partially coked catalyst, thereby producing a gaseous mixture and at least partially regenerated catalyst;
(c) recovering part of the at least partially regenerated catalyst as obtained in step (b);
(d) analysing the at least partially regenerated catalyst as obtained in step (c) to control the burning rate of the coke present on the at least partially coked catalyst in the regenerator by adjusting one or more conditions of the regeneration of the at least partially coked catalyst on the basis of the analysis of the at least partially regenerated catalyst;
(e) separating at least partially regenerated catalyst and at least part of the gaseous mixture as obtained in step (b).

The regeneration process according to the invention can contribute significantly to the overall performance of OTO-processes in terms of product yield and selectivity.

DETAILED DESCRIPTION OF THE INVENTION

In the present invention, an at least partially coked molecular sieve catalyst, in particular a catalyst as used in an oxygenate-to-olefins (OTO) process, is regenerated.

In step (a), the at least partially coked catalyst is introduced into a regenerator.

Suitably, the regeneration in step (b) is carried out at a temperature in the range of from 580-800° C., preferably in the range of from 600-750° C., more preferably in the range of from 620-680° C., and a pressure in the range of from 1-5 bara, preferably in the range of from 1-3 bara, more preferably in the range of from 1.3-2 bara.

The regeneration can suitably be carried out in a fixed bed, or a fluidized bed such as a dense, turbulent or fast fluidized bed, or in a riser regenerator. Preferably, the regeneration is carried out in a turbulent fluidized bed.

Suitably, the regeneration in step (b) can be carried out in a periodical manner or continuous manner. Preferably, the regeneration in step (b) is carried out in a continuous manner.

The residence time of the molecular sieve catalyst in the regenerator can suitably be in the range of from one minute to several hours. Preferably, the residence time is from 1 to 100 minutes. More preferably, the residence time of the catalyst in the regenerator is in the range of from 1-60 minutes, most preferably in the range of from 215 minutes.

The superficial velocity of the gas components in a dense fluidized bed will generally be from 0 to 1 m/s; the superficial velocity of the gas components in a turbulent fluidized bed will generally be from 1 to 3 m/s; the superficial velocity of the gas components in a fast fluidized bed will generally be from 3 to 5 m/s; and the superficial velocity of the gas components in a riser reactor will generally be from 5 to 25 m/s.

It will be understood that dense, turbulent and fast fluidized beds will include a dense lower reaction zone with densities generally above 300 kg/m$^3$. Moreover, when working with a fluidized bed several possible configurations can be used: (a) co-current flow meaning that the gas (going upward) and the catalyst travels through the bed in the same direction, and (b) countercurrent, meaning that the catalyst is fed at the top of the bed and travels through the bed in opposite direction with respect to the gas, whereby the catalyst leaves the vessel at the bottom. In a conventional riser reactor system the catalyst and the vapors will travel co-currently.

In order to regenerate at least part of the at least partially coked catalyst, an oxygen-containing gas is introduced in the regenerator in step (b), thereby producing a gaseous mixture and at least partially regenerated catalyst. The oxygen-containing gas may be chosen from oxygen and air. Also mixtures can suitably be used of these oxygen-containing gases. Preferably, the oxygen-containing gas comprises oxygen, more preferably air is used as the oxygen-containing gas. In specific applications, it may be preferred to increase the oxygen content of air by adding an oxygen stream or removing nitrogen from the air, with the purpose to establish an appropriate heat balance.

Suitably, the volume of oxygen in the oxygen-containing gas as introduced in step (b) is 15-50 mol-%, preferably 18-35 mol-%, based on total volume of the oxygen-containing gas.

Generally, the mass flow rate of the oxygen-containing gas may be adjusted in such a way that it satisfies the coke burn requirements from a mass balance perspective.

The amount of oxygen containing gas will be determined by the amount of coke to be removed from the catalyst and the combustion mode as applied in the regenerator. For example, if it is a partial burn mode, then oxygen containing gas will be required downstream of the regenerator in the CO boiler to complete the combustion of the CO into $CO_2$. CO cannot be released into the environment, hence, all plants will have to fully convert the CO into $CO_2$ at the end.

In step (b), suitably, between 0.01-5 wt % of the coke present on the at least partially coked catalyst is removed from the catalyst during regeneration.

Suitably, before step (a) the at least partially coked catalyst can be subject to a stripping treatment before it is introduced into to the regenerator in step (a). In such a stripping treatment a stripping gas can be used to remove organic compounds, such as non-separated olefins, from the catalyst before it is introduced into the regenerator.

In step (c), at least partially regenerated catalyst and at least part of the gaseous mixture as obtained in step (b) are separated. Typically, at least partially regenerated catalyst exits the regenerated at the bottom end, while the gaseous mixture is recovered at the top end of the regenerator. The catalyst exiting the regenerator is typically stripped to remove oxygen and other gaseous components in the gaseous mixture. Some catalyst may be entrained in the gaseous mixture and may be separated from the gaseous mixture. The latter part of the separation in step (c) can be carried out by one or more cyclone separators. Such one or more cyclone separators may be located inside, partly inside and partly outside, or outside the regenerator used. Such cyclone separators are well known in the art. Cyclone separators are preferred, but also methods for separating the catalyst from flue gas can be used that apply plates, caps, elbows, and the like.

In step (d), the at least partially regenerated catalyst as obtained in step (b) is analysed and compared to the partially coked catalyst passed to the regenerator in step (d) to control the burning rate of the coke present on the at least partially coked catalyst in the regenerator. Reference herein to the burning rate is the mass of coke removed per hour ($kg_{coke}$/hour). The burning rate of the coke is controlled by adjusting one or more operating conditions of the regeneration step of the at least partially coked catalyst on the basis of the analysis of the at least partially regenerated catalyst. In this way the level of coke on the catalyst to be recycled to a reactor can attractively be controlled. Changes in the operating conditions in the regenerator may influence the burning rate of the coke in the regenerator which may affect, when integrated with a reactor system, the overall performance and the catalyst lifetime. Such one or more operating conditions of the regeneration that can be adjusted in accordance with the present invention include the catalyst circulation time, the pressure balance in the regenerator, heat losses, the amount of coke present on the catalyst, the regeneration temperature and pressure, the mass flow rate of the oxygen-containing gas, and the level of the catalyst bed in the regenerator. Preferably, the one or more operating conditions of the regeneration step to be adjusted include at least partially coked catalyst which include the mass flow rate of the oxygen-containing gas as introduced in step (b), the residence time of the at least partially coked catalyst in the regenerator, the pressure in the regenerator and/or the regeneration temperature. Preferably, the one or more operating conditions to be adjusted include at least the mass flow rate of the oxygen-containing gas. By means of step (d) the burning rate of the coke can be controlled and optimized against changing operating conditions in the regenerator. Moreover, on the basis of the mass flow rate of the oxygen-containing gas, the analysis of the least partially regenerated catalyst and the amount of steam in the flue gas, the heat released during the regeneration can be determined, and a more direct heat control inside the regenerator can be established. In this way the overall process performance in terms of capacity and, for example, catalyst lifetime can be improved.

A sample of the at least partially regenerated catalyst to be analysed in step (d) can suitably be taken from inside the regenerator, and its composition can be analysed externally. Preferably, the sample of the at least partially regenerated catalyst is taken from the fluidized bed phase in the regenerator or the point at which regenerated catalyst exits the regeneration stage.

The analysis of the at least partially regenerated catalyst can suitably be carried out by well-known means such as Thermal Gravimetric Analysis.

The analysis of the at least partially regenerated catalyst can be done by hand or automatically, preferably automatically.

Suitably, also the gaseous mixture as obtained in step (b) is analysed to further control the burning rate of the coke present on the at least partially coked catalyst in the regenerator by adjusting one or more conditions of the regeneration of the at least partially coked catalyst also on the basis of the analysis of the gaseous mixture.

Preferably, the gaseous mixture as obtained in step (b) is also analysed to further control the burning rate of the coke present on the at least partially coked catalyst in the regenerator by adjusting the mass flow rate of the oxygen-containing gas as introduced in step (b) on the basis of the analysis of the gaseous mixture.

In such an analysis of the gaseous mixture suitably the concentration of carbon monoxide present in the gaseous mixture is determined and the burning rate of the coke present on the at least partially coked catalyst is controlled by adjusting the mass flow of the oxygen-containing gas as introduced in step (b), on the basis of the concentration of carbon monoxide present in the analysed gaseous mixture. The carbon monoxide present in the gaseous mixture results from the partial combustion of coke present on the at least partially coked catalyst.

The concentration of the carbon monoxide can suitably be determined by well-known means such as absorption spectroscopy, gas chromatography, infrared absorption spectroscopy, non-dispersive infrared analysis among others. It is further observed that that the amount of $H_2O$, $CO_2$ and $O_2$ can also be determined with these methods and they will be used for analysing the flue gas composition in order to close the mass and energy balances in the regenerator.

In another embodiment of the present invention the concentration of oxygen present in the gaseous mixture is determined for instance by continuous emission monitoring, e.g. with a $ZrO2$ oxygen analyser and the burning rate of the coke present on the at least partially coked catalyst is controlled by adjusting the mass flow rate of the oxygen-containing gas as introduced in step (b) on the basis of the concentration of oxygen present in the analysed gaseous mixture.

The oxygen present in the gaseous mixture, preferably present in the range from 0.5 to 5%, results from the full combustion of coke present on the at least partially coked catalyst.

Moisture measurements to measure water on-line can be done as well, before and after combustion.

In another embodiment of the present invention the concentrations of carbon monoxide and oxygen present in the gaseous mixture are determined and the burning rate of the coke present on the at least partially coked catalyst is controlled by adjusting the mass flow rate of the oxygen-containing gas as introduced in step (b) on the basis of the concentrations of carbon monoxide and oxygen present in the analysed gaseous mixture.

In another embodiment of the present invention the concentrations of carbon monoxide, carbon dioxide and oxygen present in the gaseous mixture are determined and the burning rate of the coke present on the at least partially coked catalyst is controlled by adjusting the mass flow rate of the oxygen-containing gas as introduced in step (b) on the basis of the concentrations of carbon monoxide, carbon dioxide and oxygen present in the analysed gaseous mixture.

In yet another embodiment of the present invention the concentrations of carbon monoxide, carbon dioxide, water and oxygen present in the gaseous mixture are determined and the burning rate of the coke present on the at least partially coked catalyst is controlled by adjusting the mass flow rate of the oxygen-containing gas as introduced in step (b) on the basis of the concentrations of carbon monoxide, carbon dioxide, water and oxygen present in the analysed gaseous mixture.

The embodiments as described hereinabove wherein the concentration of oxygen in the gaseous mixture is determined are especially attractive when the regenerator is operated in a full combustion mode of operation, resulting in a more complete oxidation of carbon monoxide and also full regeneration of catalyst inside the regenerator.

When the regenerator is operated in a partial burn mode of operation it will be sufficient to determine only the concentration of carbon monoxide in the gaseous mixture as obtained in step (b).

The analysis of the gaseous mixture can be done by hand using a gas analyser, e.g. such as those provided by Drager™ or by way of an automated analysis tool incorporated in the gas analyzers.

Preferably, the mass flow rate of the oxygen-containing gas as introduced in step (b) is automatically adjusted on the basis of the analysis of the gaseous mixture. Suitably this can be established by means of a flow control valve placed in the air line source, a compressor inlet guide vane opening or indirectly by adjusting the revolutions of a centrifugal compressor by adjusting the steam flow to the turbine coupled to the compressor.

In step (e), at least partially coked catalyst and at least part of the gaseous mixture as obtained in step (b) are separated. The separation in step (e) can be carried out by one or more cyclone separators. Such one or more cyclone separators may be located inside, partly inside and partly outside, or outside the regenerator used. Such cyclone separators are well known in the art. Cyclone separators are preferred, but also methods for separating the catalyst from flue gas can be used that apply plates, caps, elbows, and the like.

At least part of the at least partially regenerated catalyst as obtained in step (e) can be recycled to a reactor. After use in the reactor the catalyst can subsequently be introduced into the regenerator.

Since the burning of coke is an exothermic reaction, the temperature of the catalyst exiting the regenerator needs to be adjusted to the reactor requirements. This can be done in various ways. Suitably, at least part of the at least partially regenerated catalyst as obtained in step (e) is passed through a catalyst cooler before it is recycled to a reactor. In this way the temperature of the at least partially regenerated catalyst can be controlled before it is recycled to a reactor. The catalyst cooler may be a heat exchanger that is located either inside, partly inside and partly outside, or outside the regenerator. The cooled and at least partially regenerated catalyst as obtained in the catalyst cooler can be returned to the regenerator in a continuous cycle. In another embodiment a portion of the cooled and at least partially regenerated catalyst as obtained in the catalyst cooler cooled is returned to the regenerator in a continuous cycle, whereas another portion of the cooled and at least partially regenerated catalyst as obtained in the catalyst cooler is recycled to a reactor.

The regeneration process according to the present invention is suitably integrated with a reactor system, in particular with a reactor wherein an oxygenate feed is converted in an oxygenate-to-olefins (OTO) process.

In such an OTO process, an oxygenate feed is reacted in a reactor in the presence of a molecular sieve catalyst to form a mixture which comprises olefins and at least partially coked catalyst. The reactor is suitably an OTO reaction zone wherein the oxygenate feed is contacted with an oxygenate conversion catalyst under oxygenate conversion conditions, to obtain a conversion effluent comprising lower olefins. Reference herein to an oxygenate feed is to an oxygenate-comprising feed. In the OTO reaction zone, at least part of the feed is converted into a product containing one or more olefins, preferably including lower olefins, in particular ethylene and typically propylene.

The oxygenate used in such a process is preferably an oxygenate which comprises at least one oxygen-bonded alkyl group. The alkyl group preferably is a C1-C5 alkyl group, more preferably C1-C4 alkyl group, i.e. comprises 1 to 5, respectively, 4 carbon atoms; more preferably the alkyl group comprises 1 or 2 carbon atoms and most preferably one carbon atom. Examples of oxygenates that can be used in the oxygenate feed include alcohols and ethers. Examples of preferred oxygenates include alcohols, such as methanol, ethanol, propanol; and dialkyl ethers, such as dimethylether, diethylether, methylethylether. Preferably, the oxygenate is methanol or dimethylether, or a mixture thereof. More preferably, the oxygenate comprises methanol or dimethylether.

Preferably the oxygenate feed comprises at least 50 wt % of oxygenate, in particular methanol and/or dimethylether, based on total hydrocarbons, more preferably at least 70 wt %.

The oxygenate feed can comprise an amount of diluent, such as nitrogen and water, preferably in the form of steam. In one embodiment, the molar ratio of oxygenate to diluent is between 10:1 and 1:10, preferably between 4:1 and 1:2, in particular when the oxygenate is methanol and the diluent is water (steam).

A variety of OTO processes is known for converting oxygenates such as for instance methanol or dimethylether to an olefin-containing product, as already referred to above. One such process is described in WO-A 2006/020083. Processes integrating the production of oxygenates from synthesis gas and their conversion to light olefins are described in US20070203380A1 and US20070155999A1.

Catalysts suitable for use in the present regeneration process and for use in an OTO process include molecular sieve-catalysts. The molecular sieve catalyst suitably comprises one or more zeolite catalysts and/or one or more SAPO catalysts. Molecular sieve catalysts typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieve catalysts preferably have a molecular framework of one, preferably two or more corner-sharing [$TO_4$] tetrahedral units, more preferably, two or more [$SiO_4$], [$AlO_4$] and/or [$PO_4$] tetrahedral units. These silicon, aluminum and/or phosphorous based molecular sieves and metal containing silicon, aluminum and/or phosphorous based molecular sieves have been described in detail in numerous publications including for example, U.S. Pat. No. 4,567,029. In a preferred embodiment, the molecular sieve catalysts have 8-, 10- or 12-ring structures and an average pore size in the range of from about 3 Å to 15 Å.

Suitable molecular sieve catalysts are silicoaluminophosphates (SAPO), such as SAPO-17, -18, -34, -35, -44, but also SAPO-5, -8, -11, -20, -31, -36, -37, -40, -41, -42, -47 and -56; aluminophosphates (AlPO) and metal substituted (silico)aluminophosphates (MeAlPO), wherein the Me in MeAlPO refers to a substituted metal atom, including metal selected from one of Group IA, IIA, IB, IIIB, IVB, VB, VIB, VIIB, VIIIB and Lanthanide's of the Periodic Table of Elements, preferably Me is selected from one of the group consisting of Co, Cr, Cu, Fe, Ga, Ge, Mg, Mn, Ni, Sn, Ti, Zn and Zr.

Preferably, the catalyst to be used in the present regeneration process and for the conversion of the oxygenate feed comprises an aluminosilicate-comprising catalyst, in particular a zeolite-comprising catalyst. In a zeolite-comprising catalyst the amount of zeolite is suitably from 20 to 50 wt %, preferably from 35 to 45 wt %, based on total catalyst composition.

Suitable catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48.

Aluminosilicates-comprising catalyst, and in particular zeolite-comprising catalyst are preferred when an olefinic co-feed is fed to the oxygenate conversion zone together with oxygenate, for increased production of ethylene and propylene.

Preferred catalysts comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably, the channels in at least one of the directions are 10-membered ring channels. A preferred MFI-type zeolite has a Silica-to-Alumina ratio (SAR) of at least 60, preferably at least 80.

Particular catalysts include catalysts comprising one or more zeolite having one-dimensional 10-membered ring channels, i.e. one-dimensional 10-membered ring channels, which are not intersected by other channels.

Preferred examples are zeolites of the MTT and/or TON type.

In a preferred embodiment the catalyst comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11.

The catalyst may comprise phosphorus as such, i.e. in elemental form, or in a compound, i.e. phosphorous other than any phosphorus included in the framework of the molecular sieve. It is preferred that an MEL or MFI-type zeolites comprising catalyst additionally comprises phosphorus. The phosphorus may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorus as such or in a compound in an elemental amount of from 0.05-10 wt % based on the weight of the formulated catalyst. A particularly preferred catalyst comprises phosphor and MEL or MFI-type zeolites having SAR of in the range of from 60 to 150, more preferably of from 80 to 100. An even more particularly preferred catalyst comprises phosphorus and ZSM-5 having SAR of in the range of from 60 to 150, more preferably of from 80 to 100. A further particularly preferred catalyst comprises phosphorus-treated MEL or MFI-type zeolites having SAR of in the range of from 60 to 150, more preferably of from 80 to 100. An even more particularly preferred catalyst comprises phosphorus-treated ZSM-5 having SAR of in the range of from 60 to 150, more preferably of from 80 to 100.

It is preferred that the molecular sieves in the hydrogen form are used in the oxygenate conversion catalyst, e.g., HZSM-22, HZSM-23, and HZSM-48, HZSM-5. Preferably at least 50% w/w, more preferably at least 90% w/w, still more preferably at least 95% w/w and most preferably 100% of the total amount of molecular sieve used is in the hydrogen form. It is well known in the art how to produce such molecular sieves in the hydrogen form.

The catalyst particles used in the process of the present invention can have any shape known to the skilled person to be suitable for this purpose, for it can be present in the form of spray dried catalyst particles, spheres, tablets, rings, extrudates, etc. Extruded catalysts can be applied in various shapes, such as, cylinders and trilobes. Spherical particles are normally obtained by spray drying. Preferably the average particle size is in the range of 1-500 μm, preferably 50-100 μm.

The reaction conditions of the oxygenate conversion in an integrated OTO process include a reaction temperature of 350 to 1000° C., suitably from 350 to 750° C., preferably from 450 to 750° C., more preferably from 450 to 700° C., even more preferably 500 to 650° C.; and a pressure suitably from 1 bara to 50 bara, preferably from 1-15 bara, more preferably from 1-4 bara, even more preferably from 1.1-3 bara, and most preferably in from 1.3-2 bara.

Suitably, the oxygenate-comprising feed is preheated to a temperature in the range of from 120 to 550° C., preferably 250 to 500° C. prior to contacting with the molecular sieve catalyst in step (a).

Preferably, in addition to the oxygenate, an olefinic co-feed is provided along with and/or as part of the oxygenate feed. Reference herein to an olefinic co-feed is to an olefin-comprising co-feed. The olefinic co-feed preferably comprises C4 and higher olefins, more preferably C4 and C5 olefins. Preferably, the olefinic co-feed comprises at least 25 wt %, more preferably at least 50 wt %, of C4 olefins, and at least a total of 70 wt % of C4 hydrocarbon species. The olefinic co-feed can also comprise propylene.

Such an OTO process which can be integrated with the present regeneration process may suitably be operated in a fluidized bed, e.g. a dense, turbulent or fast fluidized bed or a riser reactor or downward reactor system, and also in a fixed bed reactor or a tubular reactor. A fluidized bed, e.g. a turbulent fluidized bed, fast fluidized bed or a riser reactor system are preferred.

The superficial velocity of the gas components in a dense fluidized bed will generally be from 0 to 1 m/s; the superficial velocity of the gas components in a turbulent fluidized bed will generally be from 1 to 3 m/s; the superficial velocity of the gas components in a fast fluidized bed will generally be from 3 to 5 m/s; and the superficial velocity of the gas components in a riser reactor will generally be from 5 to about 25 m/s.

It will be understood that dense, turbulent and fast fluidized beds will include a dense lower reaction zone with densities generally above 300 kg/m$^3$. Moreover, when working with a fluidized bed several possible configurations can be used: (a) co-current flow meaning that the gas (going upward) and the catalyst travels through the bed in the same direction, and (b) countercurrent, meaning that the catalyst is fed at the top of the bed and travels through the bed in opposite direction with respect to the gas, whereby the catalyst leaves the vessel at the bottom. In a conventional riser reactor system the catalyst and the vapors will travel co-currently.

More preferably, a fluidized bed, in particular a turbulent fluidized bed system is used. Suitably, in such a moving bed reactor the oxygenate feed is contacted with the molecular sieve catalyst at a weight hourly space velocity of at least 1 hr$^{-1}$, suitably from 1 to 1000 hr$^{-1}$, preferably from 1 to 500 hr$^{-1}$, more preferably 1 to 250 hr$^{-1}$, even more preferably from 1 to 100 hr$^{-1}$, and most preferably from 1 to 50 hr$^{-1}$.

Olefins and at least partially coked catalyst as obtained in an integrated OTO process are separated before the at least partially coked molecular sieve catalyst is introduced into the regenerator in step (a). The separation can be carried out by one or more cyclone separators. Such one or more cyclone separators may be located inside, partly inside and partly outside, or outside the reactor used in step (a). Such cyclone separators are well known in the art. Cyclone separators are preferred, but also methods for separating the catalyst from the olefins can be used that apply plates, caps, elbows, and the like.

Olefins obtained in an integrated OTO process will be recovered. Suitably, the recovered olefins are separated into at least one olefinic product fraction containing ethylene and/or propylene and one or more further olefinic fractions containing olefins having 4 or more carbon atoms, which further olefinic fraction(s) is (are) at least partly recycled to the OTO reaction zone for use as an olefinic co-feed.

Preferably, at least 70 wt % of the olefinic co-feed, during normal operation, is formed by the recycle stream of the one or more further olefinic fractions containing olefins having 4 or more carbon atoms, preferably at least 90 wt % of olefinic co-feed, based on the whole olefinic co-feed, is formed by such a recycle stream. In order to maximize production of ethylene and propylene, it is desirable to maximize the recycle of C4 olefins in the effluent of the OTO process. This can be done by recycling at least part of the one or more further olefinic fractions containing olefins having 4 or more carbon atoms, preferably the C4-C5 hydrocarbon fraction, more preferably the C4 hydrocarbon fraction, to the OTO reaction zone in step (a). Suitably, however, a certain part thereof, such as between 1 and 5 wt %, is withdrawn as purge, since otherwise saturated hydrocarbons, in particular C4"s (butane) would build up in an integrated OTO process, which are substantially not converted under the OTO reaction conditions.

The preferred molar ratio of oxygenate in the oxygenate feed to olefin in the olefinic co-feed provided to the integrated OTO reaction zone depends on the specific oxygenate used and the number of reactive oxygen-bonded alkyl groups therein. Preferably the molar ratio of oxygenate to olefin in the total feed lies in the range of 20:1 to 1:10, more preferably in the range of 18:1 to 1:5, still more preferably in the range of 15:1 to 1:3, even still more preferably in the range of 12:1 to 1:3.

The present regeneration process can also suitably be integrated with a reactor system in which a process is carried out that is directed at converting C4+ olefins to ethylene and propylene. Such a process is also referred to as an olefin cracking process (OCP).

In such a process suitably use is made of a zeolite-comprising catalyst. Preferably, in such a process the C4+ hydrocarbon fraction is contacted with the zeolite-comprising catalyst at a reaction temperature of 350 to 1000° C., preferably from 375 to 750° C., more preferably 450 to 700° C., even more preferably 500 to 650° C.; and a pressure from 1 bara to 50 bara, preferably from 1-15 bara. Optionally, such a stream comprising C4+ olefins also contains a diluent. Examples of suitable diluents include, but are not limited to, such as water or steam, nitrogen, paraffins and methane. Under these conditions, at least part of the olefins in the C4+ hydrocarbon fraction are converted to further ethylene and/or propylene.

In an OCP suitably aluminosilicate catalysts are used. Aluminosilicate catalysts, and in particular zeolite catalysts, have the additional advantage that in addition to the conversion of methanol or dimethylether, these catalysts also induce the conversion of olefins to ethylene and/or propylene. Therefore, aluminosilicate catalysts, and in particular zeolite catalysts, are particularly suitable for use as the catalyst in an OCP. Particular preferred catalyst for the OCP reaction, i.e. converting part of the olefinic product, and preferably part of the C4+ hydrocarbon fraction of the olefinic product including olefins, are catalysts comprising at least one zeolite selected from MFI, MEL, TON and MTT type zeolites, more preferably at least one of ZSM-5, ZSM-11, ZSM-22 and ZSM-23 zeolites.

Also an OCP process may suitably be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

The reactor and regenerator can also be arranged to allow that the oxygenate and/or olefinic feed contacts the at least partially regenerated catalyst after it is introduced into the reactor.

The at least partially regenerated catalyst can be combined with a fresh molecular sieve catalyst before it is introduced into the reactor. The at least partially regenerated catalyst can also be directly introduced into the reactor, preferably after passing through a catalyst cooler.

The at least partially regenerated catalyst can be subjected to a stripping treatment before it is introduced into the reactor. In such a stripping treatment, an inert stripping gas, such as steam or nitrogen, can be used to remove oxygen and other combustion products that might cause inconveniences in the reactor or in the products separation steps.

Suitably, a carrier, such as an inert gas, feedstock vapor, a hydrocarbon recycled stream or steam can be used semicontinuously or continuously to facilitate the introduction of the at least partially regenerated catalyst, into the reactor system. Compressed air, nitrogen or steam can be used for transporting the fresh catalyst from the fresh catalyst storage vessel into the regenerator.

The mass flow rate of the at least partially regenerated catalyst to be introduced into the reactor can be used to control the optimum level of coke on the regenerated molecular sieve catalyst. The optimum level of coke on the regenerated molecular sieve catalyst can further be controlled by means of the catalyst circulation rate, the reactor and regenerator temperature, and the residence time of the catalyst in the regenerator.

The regeneration process according to the present invention can suitably integrated with an oxygenate-to-olefins (OTO) process, but also with an olefin cracking process (OCP).

Hence, the present invention also relates to an integrated process wherein the process in accordance with the present invention is integrated with an OTO process or an OCP. In such an integrated process the OTO process or OCP is carried out in an reactor, at least part of the partially coked catalyst obtained during said process is subjected to the present regeneration process, and at least part of the at least partially regenerated catalyst as obtained in step is recycled to the OTO process or the OCP.

Therefore, the at least partially coked catalyst introduced in step (a) in the regenerator is preferably an at least partially coked molecular sieve catalyst which has been used in an oxygenate-to-olefins process or an olefin cracking process.

The present invention also provides a regeneration process, wherein at least part of the at least partially regenerated catalyst as obtained in step (c) is recycled to an oxygenate-to-olefins process or an olefin cracking process.

What is claimed is:

1. Process for the regeneration of an at least partially coked molecular sieve catalyst, which process comprises the steps of:
   (a) introducing the at least partially coked catalyst into a regenerator;
   (b) introducing into the regenerator an oxygen-containing gas to regenerate at least part of the at least partially coked catalyst by removing between 0.01-5 wt % of the coke present on the at least partially coked catalyst, thereby producing a gaseous mixture and at least partially regenerated catalyst;
   (c) recovering part of the at least partially regenerated catalyst as obtained in step (b);
   (d) analysing the at least partially regenerated catalyst as obtained in step (c) to control the burning rate of the coke present on the at least partially coked catalyst in the regenerator by adjusting one or more conditions of the regeneration of the at least partially coked catalyst on the basis of the analysis of the at least partially regenerated catalyst; and
   (e) separating at least partially regenerated catalyst and at least part of the gaseous mixture as obtained in step (b).

2. Process according to claim 1, wherein the molecular sieve catalyst comprises one or more zeolite catalysts and/or one or more SAPO, ALPO and/or MeALPO catalysts.

3. Process according to claim 1, wherein the regeneration in step (b) is carried out at a temperature in the range of from 580-800° C. and a pressure in the range of from 1-5 bara.

4. Process according to claim 1, wherein in the analysis in step (d) the amount of coke present on the at least partially regenerated catalyst is determined and the burning rate of the coke present on the at least partially coked catalyst is controlled by adjusting one or more conditions of the regeneration of the at least partially coked catalyst which include the mass flow rate of the oxygen-containing gas as introduced in step (b), the residence time of the at least partially coked catalyst in the regenerator, the pressure in the regenerator and/or the regeneration temperature on the basis of the amount of coke present on the analysed catalyst.

5. Process according to claim 1, wherein the one or more conditions of the regeneration are automatically adjusted on the basis of the analysis of the at least partially regenerated catalyst.

6. Process according to claim 1, wherein the composition of the gaseous mixture as obtained in step (b) is also analysed to control the burning rate of the coke present on the at least partially coked catalyst in the regenerator further by adjusting the one or more conditions of the regeneration of the at least partially coked catalyst also on the basis of the analysis of the gaseous mixture.

7. Process according to claims 6, wherein in the analysis of the gaseous mixture, the concentration of carbon monoxide present in the gaseous mixture is determined and the burning rate of the coke present on the at least partially coked catalyst is further controlled by adjusting the mass flow rate of the oxygen-containing gas as introduced in step (b) on the basis of the concentration of carbon monoxide present in the analysed gaseous mixture.

8. Process according to claim 6, wherein in the analysis of the gaseous mixture the concentration of oxygen present in the gaseous mixture is determined and the burning rate of the coke present on the at least partially coked catalyst is controlled by adjusting the mass flow rate of the oxygen-containing gas as introduced in step (b) on the basis of the concentration of oxygen present in the analysed gaseous mixture.

9. Process according to claim 7, wherein in the analysis of the gaseous mixture the concentration of oxygen present in the gaseous mixture is determined and the burning rate of the coke present on the at least partially coked catalyst is controlled by adjusting the mass flow rate of the oxygen-containing gas as introduced in step (b) on the basis of the concentration of oxygen present in the analysed gaseous mixture.

10. Process according to claim 1, wherein the residence time of the catalyst in the regenerator is in the range of from 0.01-60 minutes.

11. Process according to claim 1, wherein the volume of oxygen in the oxygen-containing gas as introduced in step (b) is 15-50 mol %, based on total volume of the oxygen-containing gas.

12. Process according to claim 1, wherein the at least partially coked catalyst introduced in step (a) in the regenerator is an at least partially coked molecular sieve catalyst which has been used in an oxygenate-to-olefins process or an olefin cracking process.

13. Process according to claim 12, wherein at least part of the at least partially regenerated catalyst as obtained in step (c) is recycled to the oxygenate-to-olefins process or the olefin cracking process.

* * * * *